US007872138B2

(12) United States Patent
Villani et al.

(10) Patent No.: US 7,872,138 B2
(45) Date of Patent: Jan. 18, 2011

(54) PROCESS FOR THE PREPARATION OF SUBSTITUTED-1,2,3,4-TETRAHYDROISOQUINOLINE DERIVATIVES

(75) Inventors: Frank J. Villani, Perkasie, PA (US); Hua Zhong, Basking Ridge, NJ (US)

(73) Assignee: Janssen Pharmaceutica NV (BE)

( * ) Notice: Subject to any disclaimer, the term of this patent is extended or adjusted under 35 U.S.C. 154(b) by 558 days.

(21) Appl. No.: 11/834,789

(22) Filed: Aug. 7, 2007

(65) Prior Publication Data

US 2008/0033177 A1   Feb. 7, 2008

Related U.S. Application Data

(60) Provisional application No. 60/821,601, filed on Aug. 7, 2006, provisional application No. 60/887,215, filed on Jan. 30, 2007.

(51) Int. Cl.
*C07D 401/06* (2006.01)
(52) U.S. Cl. .................................................. 546/140
(58) Field of Classification Search ........................ None
See application file for complete search history.

(56) References Cited

U.S. PATENT DOCUMENTS 3,499,901 A    3/1970   Hellerbach

FOREIGN PATENT DOCUMENTS

WO    WO 2004/103997 A1    12/2004
WO    WO 2006/018309 A1    2/2006

OTHER PUBLICATIONS

Osbond, J. M, Journal of the Chemical Society (1951) pp. 3464-3475.*
Heaney et al, Tetrahedron, (1995), 51(39), pp. 10737-10750.*
Zhong, Marlon H., et als., "Improved and Practical Synthesis of 6-Methoxy-1,2,3,4-Tetrahydroisoquinoline Hydrochloride", American Chemical Society/Organic Process Research & Development, vol. 11, No. 3, 2007, pp. 463-465.
Buck, Johannes S., "Some Substituted Tetrahydroisoquinoline Hydrochlorides", J. Am. Chem. Soc., vol. 56, 1934, pp. 1769-1771.
Craig, L.E. et al., "Curariform Activity and Chemical Structure. III Synthesis in the 3-Indolylmethylamine Series", J. Am. Chem. Soc., vol. 71, 1949, pp. 462-465.
Kalaus, Gy et al., "The Chemistry of Heterocyclic Pseudobasic Aminocarbinols, XXXVII", Acta Chimica Academiae Scientiarum Hungarica, Budapest, HU, vol. 63, No. 4, 1970, pp. 443-445.
Ruchirawat, S. et al., "A Convenient Synthesis of Simple Tetrahydroisoquinolines", Synthetic Communications, Marcel Dekker, Inc., Basel, CH, vol. 14, No. 13, 1984, pp. 1221-1228.

* cited by examiner

*Primary Examiner*—Zinna N Davis
(74) *Attorney, Agent, or Firm*—Mary A. Apollina

(57) ABSTRACT

The present invention is directed to a process for the synthesis of substituted-1,2,3,4-tetrahydroisoquinoline derivatives, useful as intermediates in the synthesis of pharmaceutical agents.

7 Claims, No Drawings

PROCESS FOR THE PREPARATION OF SUBSTITUTED-1,2,3,4-TETRAHYDROISOQUINOLINE DERIVATIVES

CROSS REFERENCE TO RELATED APPLICATION

This application claims priority from U.S. Provisional Application Ser. No. 60/821,601, filed on Aug. 7, 2006 and U.S. Provisional Application Ser. No. 60/887,215, filed on Jan. 30, 2007, the contents of which are hereby incorporated by reference in their entirety.

FIELD OF THE INVENTION

The present invention is directed to a process for the preparation of substituted-1,2,3,4-tetrahydroisoquinoline derivatives. Substituted 1,2,3,4-tetrahydroisoquinoline derivatives are useful as intermediates in the synthesis of pharmaceutical agents.

BACKGROUND OF THE INVENTION

Substituted-1,2,3,4-tetrahydroisoquinoline derivatives are useful in the synthesis of a variety of pharmaceutical agents. Synthesis of these intermediates however, has typically been difficult for a number of reasons.

For example, 6-methoxy-1,2,3,4-tetrahydroisoquinoline, although commercially available, is at present very expensive (>$400/g) and available only in milligram quantity as listed by few chemical sources. Further, although several syntheses of this compound have been reported in the literature, none are convenient to carry out on large-scale. Among the published approaches, the most direct method of tetrahydroisoquinoline formation appears to be Pictet-Spengler type condensation of 2-(3'-methoxyphenyl)ethylamine with formaldehyde (a) Whaley, W. M.; Govindachari, T. R. *Organic Reactions*, 1951, 6, 151. b) Ivanov, I., Venkov, A. *Heterocycles*, 2001, 55, 1569. c) Bates, H. A. *J. Org. Chem.*, 1983, 48, 4931-4935. d) Bates, H. A.; Bagheri, K.; Vertino, P. M. *J. Org. Chem.*, 1986, 51 3061-3063). Several research groups have used this approach to obtain the target compound in small quantity. However, the product resulting from the direct condensation of 2-(3'-methoxyphenyl)ethylamine with formaldehyde is an oil, making the isolation and purification difficult for large-scale synthesis purposes (a) Bojaeski, A. J.; Mokrosz, M. J.; Minol, S. C.; Koziol, A.; Wesolowska, A.; Tatarczynska, E.; Klodzinska, A.; Chojnacka-Wojcik, E. *Bioorg. Med. Chem.*, 2002, 10, 87-95. b) Euerby, M. R.; Waigh, R. D. *J. Chem. Res., Synopses*, 1987, 2, 36-7).

Bucks, J. S. in *J. Am. Chem. Soc.*, 1934, Vol 56., pp 1769-1771 has reported the direct isolation of a HCl salt of 6-methoxy-1,2,3,4-tetrahydroisoquinoline requiring time-consuming evaporation of aqueous HCl solution to dryness.

In addition to the direct condensation of 2-(3'-methoxyphenyl)ethylamine with formaldehyde, some approaches described in the literature required a protection of amine functionality prior to the acid-catalyzed condensation, followed by another deprotection step after the condensation. (Bojaeski, A. J.; Mokrosz, M. J.; Minol, S. C.; Koziol, A.; Wesolowska, A.; Tatarczynska, E.; Klodzinska, A.; Chojnacka-Wojcik, E. *Bioorg. Med. Chem.*, 2002, 10, 87-95; Stokker, G. E. *Tetrahedral Lett.*, 1996, 37, 5453-5456).

An alternative approach reported by Sall, D. J.; Grunewald, G. L., in *J. Med. Chem.* 1987, 30, 2208-2216 used a Fridal-Crafts type cyclization of methyl 2-(3'-methoxyphenyl)ethyl carbamate with polyphosphoric acid (PPA) to yield a mixture of 6-methoxy- and 8-methoxy-3,4-dihydroisoquinolin-one in a ratio of 2:1, respectively. After separation of the regioisomers by chromatography, lithium aluminum hydride reduction yielded the corresponding 6-methoxy- and 8-methoxy-1,2,3,4-tetrahydroisoquinoline. Although the procedure was recently utilized by Mewshaw and coworkers for their medicinal chemistry research (Meagher, K. L.; Mewshaw, R. E.; Evrard, D. A.; Zhou, P.; Smith, D. L.; Scerni, R.; Spangler, T.; Abulhawa, S.; Shi, X.; Schechter, L. E.; Andree, T. H. *Bioorg. Med. Chem. Lett.* 2001, 11, 1885-1888), the poor regioselectivity of cyclization and harsh reaction conditions prevented its application in large-scale synthesis.

Thus there remains a need for a method for the synthesis of substituted-1,2,3,4-tetrahydroisoquinoline derivatives, and more particularly, 6-methoxy-1,2,3,4-tetrahydroisoquinoline, which is suitable for large scale production.

SUMMARY OF THE INVENTION

The present invention is directed to a process for the preparation of compounds of formula (I)

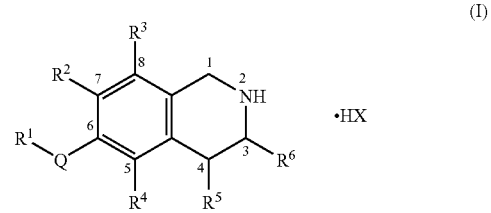

wherein

Q is selected from the group consisting of O and S;

$R^1$ is $C_{1-6}$alkyl; wherein the $C_{1-6}$alkyl is optionally substituted with one or more substituents independently selected from halogen, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino, aryl, cycloalkyl, heteroaryl or heterocycloalkyl;

wherein the aryl, cycloalkyl, heteroaryl or heterocycloalkyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

$R^2$ is selected from the group consisting of hydrogen, hydroxy, $C_{1-6}$alkyl, $C_{1-6}$alkoxy, aryl, cycloalkyl, heteroaryl or heterocycloalkyl;

wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 7-position of the 1,2,3,4-tetrahydroisoquinoline core;

alternatively, Q, $R^1$ and $R^2$ are taken together with the carbon atoms to which they are bound to form a 5 to 8 membered, monocyclic heterocycloalkyl group, wherein the 5 to 8 membered, monocyclic heterocycloalkyl optionally contains one additional heteroatom selected from O, N or S, provided that the N is not bound directly to the 7-position of the 1,2,3,4-tetrahydroisoquinoline core;

wherein the 5 to 8 membered monocyclic heterocycloalkyl is optionally substituted with one or more substituents independently selected from halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

$R^3$ and $R^4$ are each independently selected from the group consisting of hydrogen, hydroxy, $C_{1-6}$alkyl, $C_{1-6}$alkoxy, aryl, cycloalkyl, heteroaryl or heterocycloalkyl;

wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 5- or 8-position of the 1,2,3,4-tetrahydroisoquinoline core;

$R^5$ and $R^6$ are each independently selected from the group consisting of hydrogen, hydroxy, $C_{1-6}$alkyl, halogenated $C_{1-6}$alkyl, $C_{1-6}$alkoxy, halogenated $C_{1-6}$alkoxy, amino, $C_{1-4}$alkylamino, di($C_{1-4}$alkyl)amino, aryl, cycloalkyl, heteroaryl or heterocycloalkyl;

wherein the $C_{1-6}$alkyl, $C_{1-6}$alkoxy, aryl, cycloalkyl, heteroaryl or heterocycloalkyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

and HX is an inorganic acid;

comprising

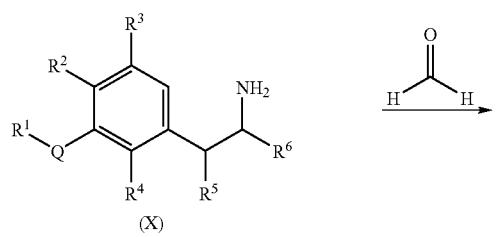

(X)

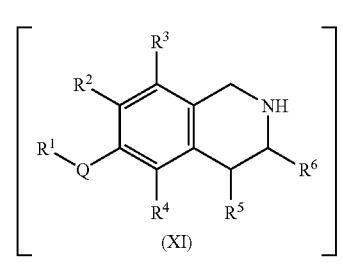

(XI)

reacting a compound of formula (X) with formaldehyde, in the presence of an inorganic acid, in water or a mixture of water and an alcohol, to yield the corresponding compound of formula (XI), which is not isolated;

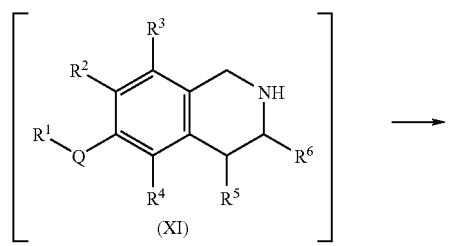

(XI)

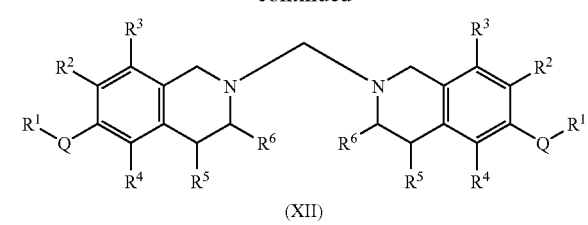

(XII)

treating the reaction mixture containing the compound of formula (XI) with an inorganic base, to yield the corresponding compound of formula (XII), which is isolated; and (XII)

(I)

reacting the compound of formula (XII) with an inorganic acid, in an alcohol, to yield the corresponding compound of formula (I).

The present invention is further directed to a process for the preparation of a compound of formula (I)

(I)

wherein Q, $R^1$, $R^2$, $R^3$, $R^4$, $R^5$, $R^6$ and HX are as herein defined, comprising

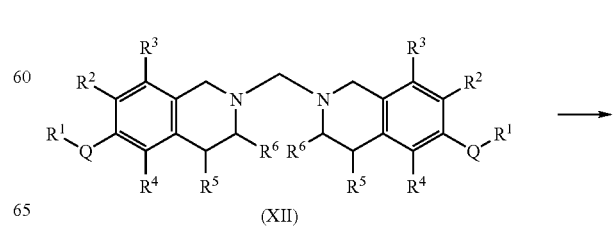

(XII)

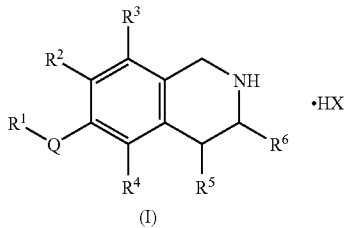

reacting a compound of formula (XII) with an inorganic acid, in an alcohol, to yield the corresponding compound of formula (I).

In an embodiment, the process for the preparation of the compound of formula (I) further comprises

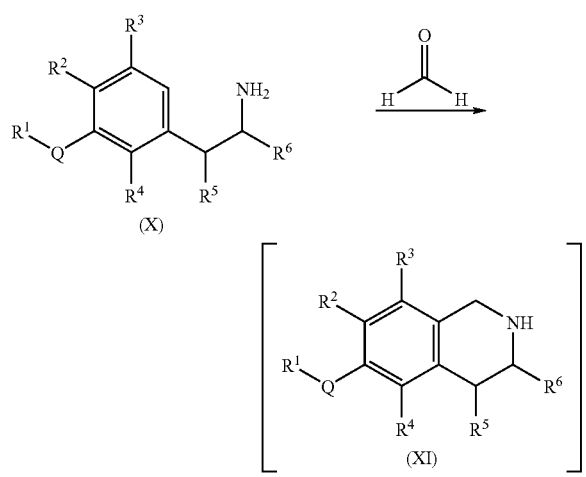

reacting a compound of formula (X) with formaldehyde, in the presence of an inorganic acid, in water or a mixture of water and an alcohol, to yield the corresponding compound of formula (XI), which is not isolated; and

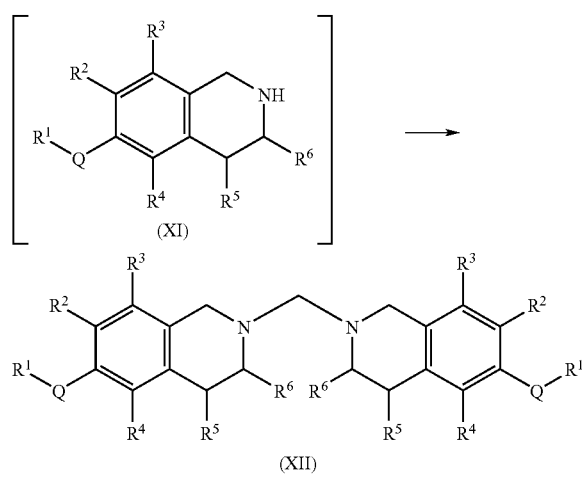

treating the reaction mixture containing the compound of formula (XI) with an inorganic base, to yield the corresponding compound of formula (XII), which is isolated.

The present invention is further directed to a compound of formula (XII)

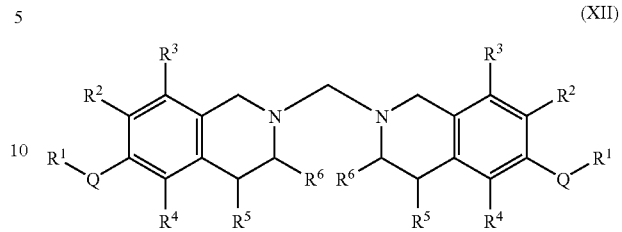

wherein

Q is selected from the group consisting of O and S;

$R^1$ is $C_{1-6}$alkyl; wherein the $C_{1-6}$alkyl is optionally substituted with one or more substituents independently selected from halogen, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino, aryl, cycloalkyl, heteroaryl or heterocycloalkyl;

wherein the aryl, cycloalkyl, heteroaryl or heterocycloalkyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

$R^2$ is selected from the group consisting of hydrogen, hydroxy, $C_{1-6}$alkyl, $C_{1-6}$alkoxy, aryl, cycloalkyl, heteroaryl or heterocycloalkyl;

wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 7-position of the 1,2,3,4-tetrahydroisoquinoline core;

alternatively, Q, $R^1$ and $R^2$ are taken together with the carbon atoms to which they are bound to form a 5 to 8 membered, monocyclic heterocycloalkyl group, wherein the 5 to 8 membered, monocyclic heterocycloalkyl optionally contains one additional heteroatom selected from O, N or S, provided that the N is not bound directly to the 7-position of the 1,2,3,4-tetrahydroisoquinoline core;

wherein the 5 to 8 membered monocyclic heterocycloalkyl is optionally substituted with one or more substituents independently selected from halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

$R^3$ and $R^4$ are each independently selected from the group consisting of hydrogen, hydroxy, $C_{1-6}$alkyl, $C_{1-6}$alkoxy, aryl, cycloalkyl, heteroaryl or heterocycloalkyl;

wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 5- or 8-position of the 1,2,3,4-tetrahydroisoquinoline core;

$R^5$ and $R^6$ are each independently selected from the group consisting of hydrogen, hydroxy, $C_{1-6}$alkyl, halogenated $C_{1-6}$alkyl, $C_{1-6}$alkoxy, halogenated $C_{1-6}$alkoxy, amino, $C_{1-4}$alkylamino, di($C_{1-4}$alkyl)amino, aryl, cycloalkyl, heteroaryl or heterocycloalkyl;

wherein the $C_{1-6}$alkyl, $C_{1-6}$alkoxy, aryl, cycloalkyl, heteroaryl or heterocycloalkyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

provided that when Q is O, $R^1$ is methyl and each of $R^3$, $R^4$, $R^5$ and $R^6$ is hydrogen, then $R^2$ is other than methoxy.

The present invention is further directed to a process for the preparation of a compound of formula (XII)

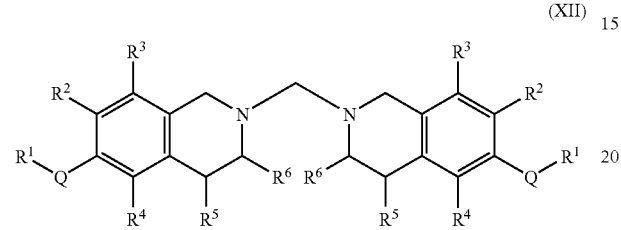

wherein Q, $R^1$, $R^2$, $R^3$, $R^4$, $R^5$, $R^6$ and HX are as herein defined, comprising

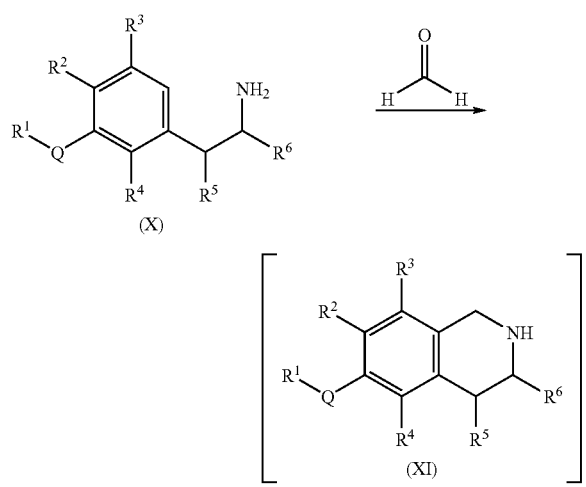

reacting a compound of formula (X) with formaldehyde, in the presence of an inorganic acid, in water or a mixture of water and an alcohol, to yield the corresponding compound of formula (XI), which is not isolated; and

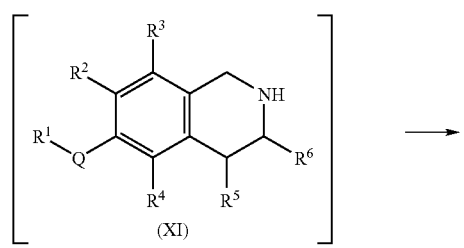

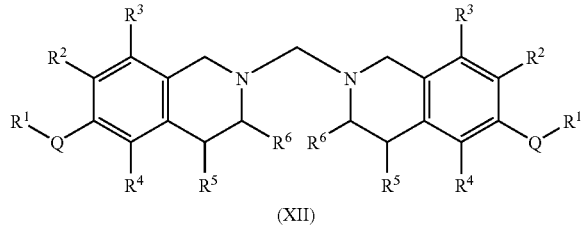

treating the reaction mixture containing the compound of formula (XI) with an inorganic base, to yield the corresponding compound of formula (XII), which is isolated.

The present invention is further directed to a product of formula (I) and/or formula (XII) prepared according to the processes described herein.

DETAILED DESCRIPTION OF THE INVENTION

The present invention is directed to processes for the preparation of compound of formula (I)

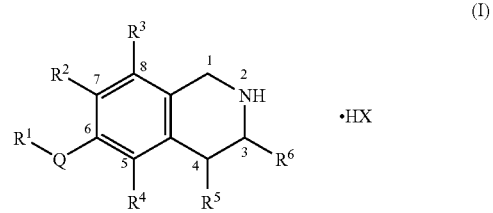

wherein Q, $R^1$, $R^2$, $R^3$, $R^4$, $R^5$, $R^6$ and HX are as herein defined. The compounds of formula (I) are useful as intermediates in the preparation of pharmaceutical agents, for example 5-HT7 receptor antagonists as disclosed by Torrens Jover, A., et al. in PCT Publication WO2006/018309 A1, published 23 Feb. 2006; PPAR-α activators as disclosed by Chang, G., in PCT Publication WO2204/103997 A1 published 2 Dec. 2004, and the like.

In an embodiment, the present invention is directed to processes for the preparation of a compound of formula (I-A)

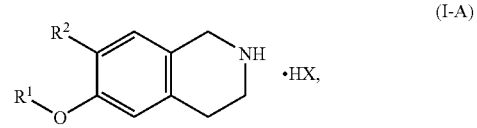

compounds of formula (I) wherein Q is O and wherein $R^3$, $R^4$, $R^5$ and $R^6$ are each hydrogen.

The present invention is further directed to compounds of formula (XII)

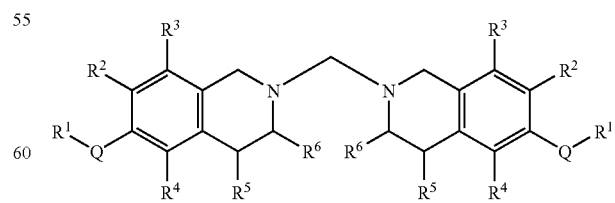

wherein Q, $R^1$, $R^2$, $R^3$, $R^4$, $R^5$ and $R^6$ are as herein defined. The compounds of formula (XII) are useful as intermediates in the preparation of the compounds of formula (I). In an embodiment of the present invention, when Q is O, $R^1$ is methyl, and each of $R^3$, $R^4$, $R^5$ and $R^6$ is hydrogen, then $R^2$ is other than methoxy. In another embodiment of the present invention, when Q is O, $R^1$ is $C_{1-4}$alkyl, $R^2$ is $C_{1-4}$alkoxy, and each of $R^3$, $R^4$, $R^5$ and $R^6$ is hydrogen, then the substituent group -Q-$R^1$ and $R^2$ are not the same. In another embodiment of the present invention, when Q is O, $R^1$ is methyl and each of $R^3$, $R^4$, $R^5$ and $R^6$ is hydrogen, then $R^2$ is selected from the group consisting of hydrogen, hydroxy, $C_{2-6}$alkyl, $C_{1-6}$alkoxy, aryl, cycloalkyl, heteroaryl or heterocycloalkyl; wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 7-position of the 1,2,3,4-tetrahydroisoquinoline core.

The present invention is further directed to a process for the preparation of compounds of formula (XII)

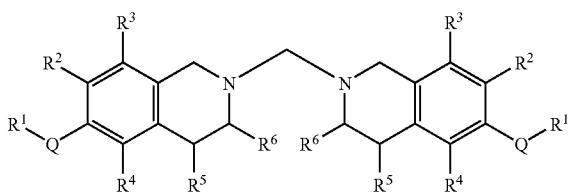

wherein Q, $R^1$, $R^2$, $R^3$, $R^4$, $R^5$ and $R^6$ are as herein defined.

In an embodiment of the present invention, Q is O. In another embodiment of the present invention Q is S. In another embodiment of the present invention Q is O and $R^3$, $R^4$, $R^5$ and $R^6$ are each hydrogen.

In an embodiment of the present invention, $R^1$ is $C_{1-4}$alkyl; wherein the $C_{1-4}$alkyl is optionally substituted with one to two substituents (preferably one substituent) independently selected from halogen, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino, phenyl, cycloalkyl, heteroaryl or heterocycloalkyl; wherein the phenyl, cycloalkyl, heteroaryl or heterocycloalkyl is optionally substituted with one to three substituents (preferably one to two substituents) selected from the group consisting of halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino.

In another embodiment of the present invention, $R^1$ is $C_{1-4}$alkyl; wherein the $C_{1-4}$alkyl is optionally substituted with one to two substituents (preferably one substituent) independently selected from halogen, $C_{1-2}$alkyl, fluorinated $C_{1-2}$alkyl, $C_{1-2}$alkoxy, fluorinated $C_{1-2}$alkoxy, amino, $C_{1-4}$alkylamino, di($C_{1-4}$alkyl)amino, phenyl or heteroaryl; wherein the phenyl or heteroaryl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino.

In another embodiment of the present invention, $R^1$ is $C_{1-4}$alkyl; wherein the $C_{1-4}$alkyl is optionally substituted with one to two substituents (preferably one substituent) independently selected from aryl, cycloalkyl, heteroaryl or heterocycloalkyl; wherein the aryl, cycloalkyl, heteroaryl or heterocycloalkyl is optionally substituted with one to three substituents (preferably one to two substituents) selected from the group consisting of halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino.

In another embodiment of the present invention, $R^1$ is $C_{1-4}$alkyl, preferably, $R^1$ is ethyl or methyl, more preferably, $R^1$ is methyl.

In an embodiment of the present invention, $R^2$ is selected from the group consisting of hydrogen, hydroxy, $C_{1-4}$alkyl, $C_{1-4}$alkoxy, phenyl, cycloalkyl, heteroaryl or heterocycloalkyl; wherein the $C_{1-4}$alkyl, $C_{1-4}$alkoxy, phenyl, cycloalkyl, heteroaryl or heterocycloalkyl is optionally substituted with one to three substituents (preferably one to two substituents) independently selected from the group consisting of hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino and halogen.

In another embodiment of the present invention, $R^2$ is selected from the group consisting of hydrogen, hydroxy, $C_{1-4}$alkyl, $C_{1-4}$alkoxy, phenyl or heteroaryl; wherein the $C_{1-4}$alkyl, $C_{1-4}$alkoxy, phenyl or heteroaryl is optionally substituted with one to three substituents (preferably one to two substituents) independently selected from the group consisting of hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino and halogen.

In another embodiment of the present invention, $R^2$ is selected from the group consisting of hydrogen, $C_{1-4}$alkyl, $C_{1-4}$alkoxy, aryl, cycloalkyl, heteroaryl or heterocycloalkyl; wherein the $C_{1-4}$alkyl, $C_{1-4}$alkoxy, aryl, cycloalkyl, heteroaryl or heterocycloalkyl is optionally substituted with one to three substituents (preferably one to two substituents) independently selected from the group consisting of hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino and halogen.

In another embodiment of the present invention, $R^2$ is selected from the group consisting of hydrogen and methoxy.

In an embodiment of the present invention, Q, $R^1$ and $R^2$ are taken together with the carbon atoms to which they are bound to form a 5 to 8 membered, monocyclic heterocycloalkyl group, wherein the 5 to 8 membered, monocyclic heterocycloalkyl optionally contains one additional heteroatom selected from O, N or S, provided that the N is not bound directly to the 7-position of the 1,2,3,4-tetrahydroisoquinoline core; wherein the 5 to 8 membered monocyclic heterocycloalkyl is optionally substituted with one to three substituents (preferably one to two substituents) independently selected from halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino;

In another embodiment of the present invention, Q, $R^1$ and $R^2$ are taken together with the carbon atoms to which they are bound to form a 5 to 6 membered, monocyclic heterocycloalkyl. In another embodiment of the present invention, Q, $R^1$ and $R^2$ are taken together with the carbon atoms to which they are bound to form a 5 to 6 membered monocyclic heterocycloalkyl optionally containing one additional heteroatom selected from O or N.

In another embodiment of the present invention, Q, $R^1$ and $R^2$ are taken together with the carbon atoms to which they are bound to form 1,3-dioxolanyl.

In an embodiment of the present invention, $R^3$ and $R^4$ are each independently selected from the group consisting of hydrogen, hydroxy, $C_{1-4}$alkyl, $C_{1-4}$alkoxy, phenyl, cycloalkyl, heteroaryl or heterocycloalkyl; wherein the $C_{1-4}$alkyl, $C_{1-4}$alkoxy, phenyl, cycloalkyl, heteroaryl or heterocycloalkyl is optionally substituted with one to three substituents (preferably one to two substituents) independently selected from the group consisting of hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino and halogen.

In another embodiment of the present invention $R^3$ and $R^4$ are each independently selected from the group consisting of hydrogen, hydroxy, $C_{1-4}$alkyl, $C_{1-4}$alkoxy, phenyl or heteroaryl; wherein the $C_{1-4}$alkyl, $C_{1-4}$alkoxy, phenyl or heteroaryl is optionally substituted with one to three substituents (preferably one to two substituents) independently selected from the group consisting of hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino and halogen.

In another embodiment of the present invention, $R^3$ and $R^4$ are each independently selected from the group consisting of hydrogen, hydroxy, $C_{1-4}$alkyl, $C_{1-4}$alkoxy, phenyl, 5 to 6 membered cycloalkyl, monocyclic heteroaryl or monocyclic heterocycloalkyl; wherein the $C_{1-4}$alkyl, $C_{1-4}$alkoxy, phenyl, 5 to 6 membered cycloalkyl, monocyclic heteroaryl or monocyclic heterocycloalkyl is optionally substituted with one to three substituents (preferably one to two substituents) independently selected from the group consisting of hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino and halogen.

In another embodiment of the present invention $R^3$ and $R^4$ are each hydrogen.

In an embodiment of the present invention, $R^5$ and $R^6$ are each independently selected from the group consisting of hydrogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino, phenyl, cycloalkyl, heteroaryl or heterocycloalkyl; wherein the $C_{1-4}$alkyl, $C_{1-4}$alkoxy, phenyl, cycloalkyl, heteroaryl or heterocycloalkyl is optionally substituted with one to three substituents (preferably one to two substituents) independently selected from the group consisting of halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino.

In another embodiment of the present invention, $R^5$ and $R^6$ are each independently selected from the group consisting of hydrogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino, phenyl or heteroaryl; wherein the $C_{1-4}$alkyl, $C_{1-4}$alkoxy, phenyl or heteroaryl is optionally substituted with one to three substituents (preferably one to two substituents) independently selected from the group consisting of halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino.

In another embodiment of the present invention, $R^5$ and $R^6$ are each independently selected from the group consisting of hydrogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino, di($C_{1-4}$alkyl)amino, phenyl, 5 to 6 membered cycloalkyl, monocyclic heteroaryl or monocyclic heterocycloalkyl; wherein the $C_{1-4}$alkyl, $C_{1-4}$alkoxy, phenyl, 5 to 6 membered cycloalkyl, monocyclic heteroaryl or monocyclic heterocycloalkyl is optionally substituted with one to three substituents (preferably one to two substituents) independently selected from the group consisting of halogen, hydroxy, $C_{1-4}$alkyl, fluorinated $C_{1-4}$alkyl, $C_{1-4}$alkoxy, fluorinated $C_{1-4}$alkoxy, amino, $C_{1-4}$alkylamino and di($C_{1-4}$alkyl)amino.

In another embodiment of the present invention, $R^5$ and $R^6$ are each hydrogen.

In an embodiment of the present invention, HX is an inorganic acid selected from the group consisting of HCl, HBr and $H_2SO_4$. In another embodiment of the present invention, HX is selected from the group consisting of HCl and HBr. Preferably, HX is HCl.

In an embodiment, the present invention is directed to a process for the preparation of 6-methoxy-1,2,3,4-tetrahydroisoquinoline. In another embodiment, the present invention is directed to a process for the preparation of 6,7-dimethoxy-1,2,3,4-tetrahydroisoquinoline. In another embodiment, the present invention is directed to a process for the preparation of 5,6,7,8-tetrahydro-[1,3]dioxolo[4,5-g]isoquinoline.

As used herein, "halogen" shall mean chlorine, bromine, fluorine and iodine. Preferably, the halogen is selected from chlorine, bromine or fluorine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-6}$" when used with alkyl means a straight or branched carbon chain composition of 1-6 carbon atoms. In an embodiment of the present invention, alkyl, whether alone or as part of a substituent group is selected from methyl, ethyl or t-butyl.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CH_2$—$CF_3$, —$CF_2$—$CF_2$—$CF_2$—$CF_3$, and the like. Similarly, the term "fluorinated $C_{1-4}$alkyl" shall mean any $C_{1-4}$alkyl group as defined above substituted with at least one fluorine atom, preferably at least three fluorine atoms. Suitable examples include but are not limited to —$CF_3$, —$CH_2$—$CF_3$, —$CF_2$—$CF_2$—$CF_2$—$CF_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{1-6}$" when used with alkyl means an oxygen ether radical of a straight or branched carbon chain composition of 1-6 carbon atoms.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —$OCF_3$, —$OCH_2$—$CF_3$, —$OCF_2$—$CF_2$—$CF_2$—$CF_3$, and the like. Similarly, the term "fluorinated $C_{1-4}$alkoxy" shall mean any $C_{1-4}$alkyl group as defined above substituted with at least one fluorine atom, preferably at least three fluorine atoms. Suitable examples include but are not limited to —$CF_3$, —$CH_2$—$CF_3$, —$CF_2$—$CF_2$—$CF_2$—$CF_3$, and the like.

As used herein, unless otherwise noted, "aryl" shall refer to unsubstituted carbocylic aromatic groups such as phenyl, naphthyl, and the like. Preferably, the aryl, whether substituted or unsubstituted is phenyl or naphthyl, more preferably, phenyl.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl. Preferably, the cycloalkyl group is cyclopentyl or cyclohexyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to eight membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

When a particular group is "substituted" (e.g., alkyl, alkoxy, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

One skilled in the art will recognize that in drawings of the structure of the compounds of formula (I), for example as shown below

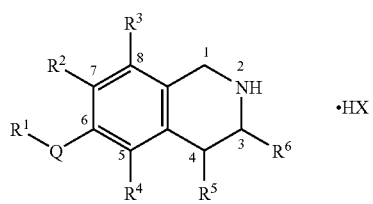

the numbers around the 1,2,3,4-tetrahydroisoquinolinyl core are intended to provide guidance as to the numbering of the position at which the Q-$R^1$, $R^2$, $R^3$, $R^4$, $R^5$ and $R^6$ substituent groups are bound to the 1,2,3,4-tetrahydroisoquinolinyl core.

As used herein, unless otherwise noted, the term "antisolvent" shall refer to a solvent which does not dissolve a specific substance and is added to a solution of said substance, directly or by vapor diffusion, to cause precipitation of said substance.

The present invention is directed to a process for the preparation of compounds of formula (I), as outlined in more detail in Scheme 1 below.

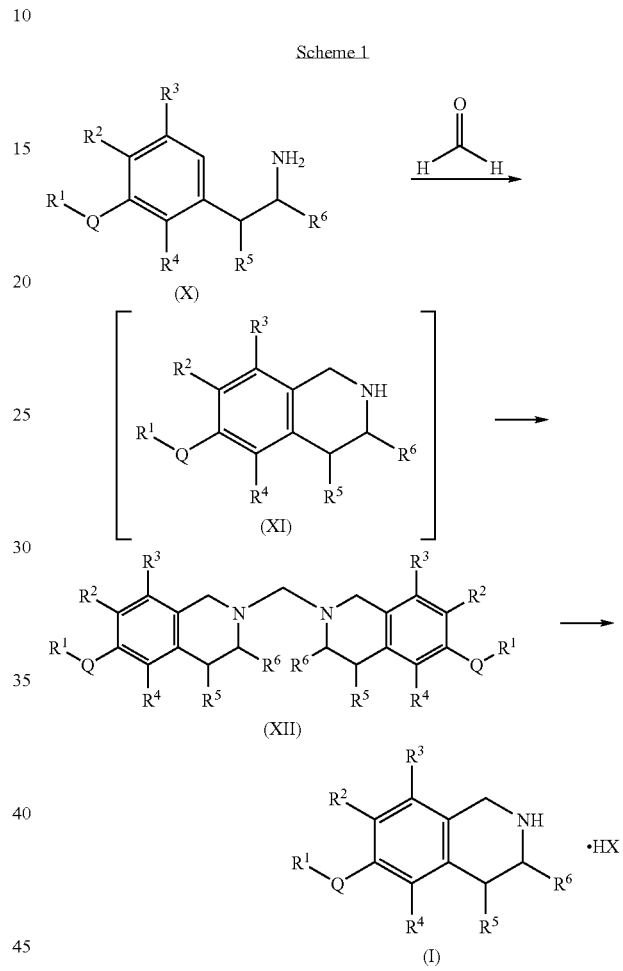

Accordingly, a suitably substituted compound of formula (X), a known compound or compound prepared by known methods, is reacted with formaldehyde, a known compound, wherein the formaldehyde is present in an amount in the range of from about 2 to about 10 molar equivalents (relative to the amount of the compound of formula (X), preferably, the formaldehyde is present in an amount in a range of from about 4 to about 5 molar equivalents;

in the presence of an inorganic acid such as HCl, HBr, $H_2SO_4$, and the like, wherein the acid is present in an amount in the range of from about 1 to about 4 molar equivalents (relative to the amount of the compound of formula (X)), preferably, the acid is present in an amount in a range of from about 1.2 to about 2 molar equivalents;

in a solvent such as water, or a mixture of water and an alcohol, such as a mixture of methanol and water, ethanol and water, and the like; at a temperature in the range of from about room temperature to about 100° C., preferably at a temperature in the in the range of from about 40° C. to about 60° C.;

to yield the corresponding compound of formula (XI). The compound of formula (XI) is not isolated.

The reaction mixture containing the compound of formula (XI) is treated with an inorganic base such as NaOH, KOH, LiOH, and the like, to a pH greater than or equal to about 9, preferably to a pH in the range of about 9 to about 14, more preferably, to a pH in the range of about 11 to about 12; at a temperature in the range of from about room temperature to about 60° C., preferably at a temperature in the in the range of from about 25° C. to about 30° C.; to yield the corresponding compound of formula (XII).

The compound of formula (XII) is isolated and optionally purified according to known methods. For example, the compound of formula (XII) may be isolated according to known methods, for example by evaporation of the solvent, by filtration, or other suitable method. Preferably, the compound of formula (XII) is isolated by filtration. The compound of formula (XII) may be further purified according to known methods, for example by chromatography, recrystallization or other suitable method.

The compound of formula (XII) is reacted with an inorganic acid (HX) such as HCl, HBr, $H_2SO_4$, and the like, wherein the acid is present in an amount in the range of from about 1 to about 4 molar equivalents (relative to the amount of the compound of formula (XII), preferably, the acid is present in an amount in a range of from about 2 to about 2.5 molar equivalents;
in an alcohol such as isopropyl alcohol (IPA), ethanol (EtOH), methanol (MeOH), and the like, at a temperature in the range of from about 0° C. to about 60° C., preferably at a temperature in the in the range of from about 20° C. to about 25° C. to yield the corresponding compound of formula (I).

The compound of formula (I) is isolated according to known methods. For example, the compound of formula (I) may be isolated by evaporation of the solvent, by filtration or other suitable method. Preferably, the compound of formula (I) is isolated by addition of a anti-solvent (i.e. a solvent which affects precipitation of the product) to the reaction mixture. For example, by addition of a non-polar organic solvent such as methyl t-butyl ether (MTBE), ethyl acetate, and the like. The compound of formula (I) may be further purified according to known methods, by for example chromatography, recrystallization or other suitable method.

One skilled in the art will recognize that the $R^1$, $R^2$, $R^3$, $R^4$, $R^5$ and $R^6$ groups and any substituents on $R^1$, $R^2$, $R^3$, $R^4$, $R^5$ and $R^6$ groups are selected to be stable (i.e. un-reactive) under strong acid and base conditions. Preferably the substituent groups are stable at a pH<about 2, and at a pH>about 11, more preferably at a pH<about 1; and at preferably, pH>about 12.

One skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples are set forth to aid in the understanding of the invention, and are not intended and should not be construed to limit in any way the invention set forth in the claims which follow thereafter.

All reagents and solvents were used directly as purchased from commercial suppliers. $^1$H-NMR and $^{13}$C-NMR spectra were recorded at 300 MHz using Bruker Avance-300. Mass Spectra were performed on Fannigan Navigator MS. Elemental analyses were provided by Robertson Microlit Laboratories, Inc.

Example 1

Bis(6-methoxy-3,4-dihydroisoquinolin-2(1H)-yl) methane

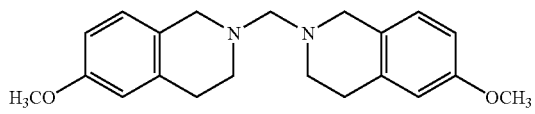

An aqueous solution of formaldehyde (416.5 g, 37% wt., 5.13 mol) was added to a solution of 2-(3-methoxyphenyl) ethylamine (200.0 g, 1.28 mol) in an aqueous 1 N HCl solution (1.92 L, 1.92 mol). The reaction mixture was stirred at 60° C. for 1 hour. The reaction mixture was then cooled to room temperature and basified with 50% NaOH solution (174.4 g, 2.18 mol) in the following order:

(a) 40% of the total amount of NaOH solution was added slowly over 10 minutes and the internal reaction temperature was maintained in the range of 25-30° C. by using an ice-water batch. The resulting light suspension was then stirred at a temperature in the range of 25-30° C. for 1 hour.

(b) Another 15% of the total amount of NaOH solution was then slowly added over 5 minutes while maintaining the internal temperature of the reaction mixture in the range of 25-30° C. The resulting light suspension was stirred at a temperature in the range of 25-30° C. for 1 hour.

(c) Another 15% of the total amount of NaOH solution was added slowly over 5 minutes while maintaining the internal reaction temperature in the range of 25-30° C. The resulting light suspension was stirred at a temperature in the range of 25-30° C. for 1 hour.

(d) The remaining 30% of NaOH solution was added slowly over 5 minutes while maintaining the internal temperature of the reaction mixture in the range of 25-30° C.

After addition of all of the NaOH solution, the resulting heavy suspension was stirred at a temperature in the range of 25-30° C. for 2 hours. The resulting solid product was collected by vacuum filtration, washed with $H_2O$ (200 mL), and air-dried. The title compound was obtained as a white solid.

Melting Point: 121° C. (by DSC analysis)

$^1$H NMR (300 MHz, $CDCl_3$): δ 6.95 (d, J=8.4 Hz, 2H), 6.70 (dd, J=8.4, 2.6 Hz, 2H), 6.65 (d, J=2.5 Hz, 2H), 3.77 (s, 6H), 3.25 (s, 2H), 3.23 (s, 4H), 2.85 (m, 8H)

$^{13}$C NMR (300 MHz, $CDCl_3$): δ 157.9, 136.0, 127.6, 127.3, 113.3, 112.0, 80.7, 55.2, 53.9, 49.0, 29.4

Elemental Analysis for $C_{21}H_{26}N_2O_2$:
Calculated: C, 74.52; H, 7.74; N, 8.21.
Measured: C, 74.20; H, 7.95; N, 8.11.

Example 2

6-Methoxytetrahydroisoquinoline HCl salt

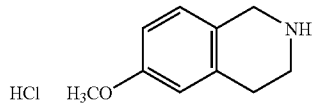

Bis(6-methoxy-3,4-dihydroisoquinolin-2(1H)-yl)methane, prepared as in Example 1 above (213.4 g, 0.63 mol) was suspended in IPA (1.06 L), to which a concentrated aqueous HCl solution (140.4 g, 36% wt., 1.38 mol) was added slowly. Most of the solids were dissolved immediately after the addition of HCl. A solid was re-precipitated in a few seconds afterwards. The resulting suspension was stirred at room temperature for 18 hours. MTBE (530 mL) was added and the suspension was stirred at room temperature for an additional 4 hours. The solid was filtered, rinsed with a 1:1 mixture of MTBE:IPA (100 mL), and then air-dried. The title compound was obtained as a white solid.

Melting Point: 239° C. (by DSC analysis)
$^1$H NMR (300 MHz, DMSO-d$^6$): δ 7.13 (d, J=8.4 Hz, 1H), 6.81 (d, J=8.4, 2.6 Hz, 1H), 6.79 (s, 1H), 3.77 (s, 6H), 4.14 (br s, 2H), 3.73 (s, 3H), 3.10 (br m, 2H), 2.50 (t, J=1.6 Hz, 2H)
$^{13}$C NMR (300 MHz, DMSO-d$^6$): δ 158.8, 133.7, 128.2, 121.2, 113.5, 113.4, 55.5, 43.4, 40.7, 25.3
Elemental Analysis for $C_{10}H_{14}NOCl$:
Calculated: C, 60.15; H, 7.07; N, 7.01; Cl, 17.76.
Measured: C, 60.23; H, 7.27; N, 6.88; Cl, 17.89.

Example 3

Bis(7,8-dihydro-[1,3]dioxolo[4,5-g]isoquinolin-6 (5H)-yl)methane

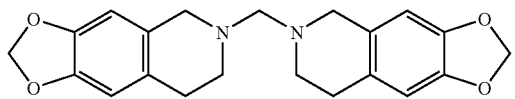

An aqueous solution of formaldehyde (4.165 g, 37% wt., 51.3 mmol) was added to a solution of 3,4-methylenedioxyphenethylamine HCl (2.158 g, 98% wt., 10.5 mmol) in an aqueous 1 N HCl solution (19.2 mL, 19.2 mmol). The reaction mixture was stirred at 40° C. for 18 hours. The reaction mixture was then cooled to room temperature and basified with an aqueous 3 N NaOH solution (7.3 mL, 21.8 mmol) in portions as follows: (a) 40% of the total amount of NaOH solution was added slowly over 10 minutes, and the resulting light suspension was stirred at 25-30° C. for 1 hour; (b) 15% of the total amount of NaOH solution was added slowly over 5 minutes, and the resulting light suspension was stirred at 25-30° C. for 1 hour; (c) another 15% of the total amount of NaOH solution was added slowly over 5 minutes, and the resulting light suspension was stirred at 25-30° C. for 1 hour; (d) the final 30% of the total amount of NaOH solution was added slowly over 5 minutes, and the resulting heavy suspension was stirred at 25-30° C. for 2 hours. The solid product was collected by vacuum filtration, washed with distilled water (2.0 mL), and air-dried overnight to yield the title compound as a fine pale peach solid.

Melting Point: 116.32° C. (by DSC analysis)
$^1$H-NMR (300 MHz, CDCl$_3$): δ6.57 (s, 2H), 6.50 (s, 2H), 5.89 (s, 4H), 3.63 (s, 4H), 3.23 (s, 2H), 2.80 (s, 8H)
$^{13}$C-NMR (300 MHz, CDCl$_3$): δ 145.9, 145.6, 127.8, 127.7, 108.5, 106.6, 106.4, 100.5, 80.4, 54.4, 49.1, 29.0
Elemental Analysis for $C_{21}H_{22}N_2O_4$:
Calculated: C, 68.84; H, 6.05; N, 7.65.
Measured: C, 68.58; H, 6.10; N, 7.48.

Example 4

5,6,7,8-Tetrahydro-[1,3]dioxolo[4,5-g]isoquinoline HCl Salt

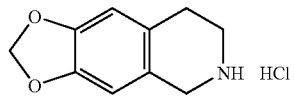

Bis(7,8-dihydro-[1,3]dioxolo[4,5-g]isoquinolin-6(5H)-yl)methane, prepared as in Example 3 above (1.791 g, 4.9 mmol) was suspended in IPA (15.8 mL), and a concentrated aqueous HCl solution (1.293 g, 36% wt., 12.7 mmol) was added slowly. The compound prepared as in Example 3 was dissolved immediately after the addition of HCl, and then a solid re-precipitated after a few seconds of stirring. The resulting suspension was stirred at room temperature for 18 hours. MTBE (7.9 mL) was added, and the suspension was stirred at room temperature for an additional 4 hours. The solid product was collected by vacuum filtration, washed with a 1/1 mixture of IPA/MTBE (10.0 mL), and air-dried overnight to yield the title compound as a fine white solid.

Melting Point: decomposes at 265.0° C.
Elemental Analysis for $C_{10}H_{11}NO_2 \cdot HCl \cdot 0.26H_2O$:
Calculated: C, 56.21; H, 5.66; N, 6.56; Cl, 16.59.
Measured: C, 55.33; H, 5.62; N, 6.06; Cl, 16.21.

Example 5

Bis(6,7-dimethoxy-3,4-dihydroisoquinolin-2(1H)-yl) methane

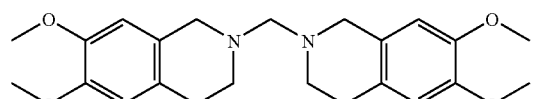

An aqueous solution of formaldehyde (4.165 g, 37% wt., 51.3 mmol) was added to a solution of 2-(3,4-dimethoxyphenyl)ethylamine (2.391 g, 97% wt., 12.8 mmol) in an aqueous 1 N HCl solution (19.2 mL, 19.2 mmol). The reaction mixture was stirred at 60° C. for 2 hours. The reaction mixture was then cooled to room temperature and basified with an aqueous 3 N NaOH solution (7.3 mL, 21.8 mmol) in portions as follows: (a) 40% of the total amount of NaOH solution was added slowly over 10 minutes, and the resulting light suspension was stirred at 25-30° C. for 1 hour; (b) 15% of the total amount of NaOH solution was added slowly over 5 minutes, and the resulting light suspension was stirred at 25-30° C. for 1 hour; (c) another 15% of the total amount of NaOH solution was added slowly over 5 minutes, and the resulting light suspension was stirred at 25-30° C. for 1 hour; (d) the final 30% of the total amount of NaOH solution was added slowly over 5 minutes, and the resulting heavy suspension was stirred at 25-30° C. for 2 hours. The solid product was collected by vacuum filtration, washed with distilled water (2.0 mL), and air-dried overnight to yield the title compound as a fine pale yellow solid.

Melting Point: 126.23° C. (by DSC analysis).

$^1$H-NMR (300 MHz, CDCl$_3$): δ6.61 (s, 2H), 6.55 (s, 2H), 3.84 (d, J=19.9 Hz, 12H), 3.67 (s, 4H), 3.27 (s, 2H), 2.84 (s, 8H)

$^{13}$C-NMR (300 MHz, CDCl$_3$): 147.4, 147.2, 126.9, 126.6, 111.5, 109.6, 80.6, 55.9, 55.9, 54.0, 49.1, 28.6

Elemental Analysis for C$_{23}$H$_{30}$N$_2$O$_4$:
Calculated: C, 69.32; H, 7.59; N, 7.03.
Measured: C, 69.20; H, 7.40; N, 6.96.

Example 6

6,7-Dimethoxy-1,2,3,4-tetrahydro-isoquinoline HCl Salt

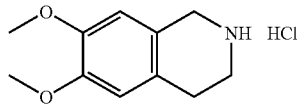

Bis(6,7-dimethoxy-3,4-dihydroisoquinolin-2(1H)-yl) methane, prepared as in Example 5 above (2.159 g, 5.4 mmol) was suspended in IPA (9.5 mL), and a concentrated aqueous HCl solution (1.279 g, 36% wt., 12.6 mmol) was added slowly. The solid starting material dissolved immediately after the addition of HCl, and then a solid re-precipitated after a few seconds of stirring. The resulting suspension was stirred at room temperature for 18 hours. MTBE (10 mL) was added, and the suspension was stirred at room temperature for an additional 4 hours. The solid product was collected by vacuum filtration, washed with a 1/1 mixture of IPA/MTBE (1.0 mL), and air-dried overnight to yield the title compound as a fine white solid.

Melting Point: 246.45° C. (by DSC analysis).
Elemental Analysis for C$_{11}$H$_{15}$NO$_2$.HCl:
Calculated: 57.52; H, 7.02; N, 6.10; Cl, 15.43.
Measured: C, 57.50; H, 7.02; N, 5.97; Cl, 15.27.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (XII)

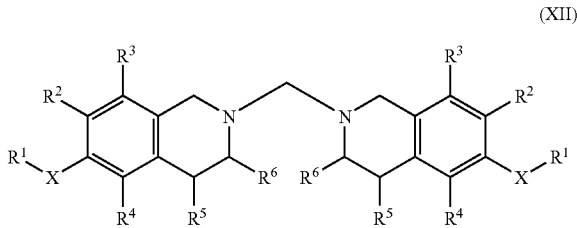

(XII)

wherein
Q is selected from the group consisting of O and S;
R$^1$ is C$_{1-6}$alkyl; wherein the C$_{1-6}$alkyl is optionally substituted with one or more substituents independently selected from halogen, C$_{1-4}$alkyl, halogenated C$_{1-4}$alkyl, C$_{1-4}$alkoxy, halogenated C$_{1-4}$alkoxy, amino, C$_{1-4}$alkylamino, di(C$_{1-4}$alkyl)amino, aryl, cycloalkyl, heteroaryl or heterocycloalkyl;
wherein the aryl, cycloalkyl, heteroaryl or heterocycloalkyl is optionally substituted with one or more substituents independently selected from the group consisting of halogen, hydroxy, C$_{1-4}$alkyl, halogenated C$_{1-4}$alkyl, C$_{1-4}$alkoxy, halogenated C$_{1-4}$alkoxy, amino, C$_{1-4}$alkylamino and di(C$_{1-4}$alkyl)amino;
R$^2$ is selected from the group consisting of hydrogen, hydroxy, C$_{1-6}$alkyl, C$_{1-6}$alkoxy, aryl, cycloalkyl, heteroaryl or heterocycloalkyl;
wherein the C$_{1-6}$alkyl, C$_{1-6}$alkoxy, aryl, cycloalkyl, heteroaryl or heterocycloalkyl is optionally substituted with one or more substituents independently selected from the group consisting of halogen, hydroxy, C$_{1-4}$alkyl, halogenated C$_{1-4}$alkyl, C$_{1-4}$alkoxy, halogenated C$_{1-4}$alkoxy, amino, C$_{1-4}$alkylamino and di(C$_{1-4}$alkyl)amino;
provided that the halogen is not bound to a carbon atom that is bound directly to the 7-position of the 1,2,3,4-tetrahydroisoquinoline core;
alternatively, Q, R$^1$ and R$^2$ are taken together with the carbon atoms to which they are bound to form a 5 to 8 membered, monocyclic heterocycloalkyl group, wherein the 5 to 8 membered, monocyclic heterocycloalkyl optionally contains one additional heteroatoms selected from O, N or S; provided that the N is not bound directly to the 7-position of the 1,2,3,4-tetrahydroisoquinoline core;
wherein the 5 to 8 membered monocyclic heterocycloalkyl is optionally substituted with one or more substituents independently selected from halogen, hydroxy, C$_{1-4}$alkyl, halogenated C$_{1-4}$alkyl, C$_{1-4}$alkoxy, halogenated C$_{1-4}$alkoxy, amino, C$_{1-4}$alkylamino and di(C$_{1-4}$alkyl)amino;
R$^3$ and R$^4$ are each independently selected from the group consisting of hydrogen, hydroxy, C$_{1-6}$alkyl, C$_{1-6}$alkoxy, aryl, cycloalkyl, heteroaryl or heterocycloalkyl;
wherein the C$_{1-6}$alkyl, C$_{1-6}$alkoxy, aryl, cycloalkyl, heteroaryl or heterocycloalkyl is optionally substituted with one or more substituents independently selected from the group consisting of halogen, hydroxy, C$_{1-4}$alkyl, halogenated C$_{1-4}$alkyl, C$_{1-4}$alkoxy, halogenated C$_{1-4}$alkoxy, amino, C$_{1-4}$alkylamino and di(C$_{1-4}$alkyl)amino;
provided that the halogen is not bound to a carbon atom that is bound directly to the 5- or 8-position of the 1,2,3,4-tetrahydroisoquinoline core;
R$^5$ and R$^6$ are each independently selected from the group consisting of hydrogen, hydroxy, C$_{1-6}$alkyl, halogenated C$_{1-6}$alkyl, C$_{1-6}$alkoxy, halogenated C$_{1-6}$alkoxy, amino, C$_{1-4}$alkylamino, di(C$_{1-4}$alkyl)amino, aryl, cycloalkyl, heteroaryl or heterocycloalkyl;
wherein the C$_{1-6}$alkyl, C$_{1-6}$alkoxy, aryl, cycloalkyl, heteroaryl or heterocycloalkyl is optionally substituted with one or more substituents independently selected from the group consisting of halogen, hydroxy, C$_{1-4}$alkyl, halogenated C$_{1-4}$alkyl, C$_{1-4}$alkoxy, halogenated C$_{1-4}$alkoxy, amino, C$_{1-4}$alkylamino and di(C$_{1-4}$alkyl)amino;
provided that when Q is O, R$^1$ is methyl and each of R$^3$, R$^4$, R$^5$ and R$^6$ is hydrogen, then R$^2$ is other than methoxy.
2. A compound as in claim 1, wherein
Q is O; and
each of R$^3$, R$^4$, R$^5$ and R$^6$ are hydrogen;

provided that when R¹ is methyl, then R² is other than methoxy.

3. A compound as in claim 1, wherein
Q is O;
R¹ is methyl;
R² is selected from the group consisting of hydrogen or methoxy;
alternatively Q, R¹ and R² are taken together with the carbon atoms to which they are bound to form 1,3-dioxolanyl; and
each of R³, R⁴, R⁵ and R⁶ is hydrogen;
provided that when Q is O and R¹ is methyl, then R² is other than methoxy.

4. A process for the preparation of a compound of formula (XII)

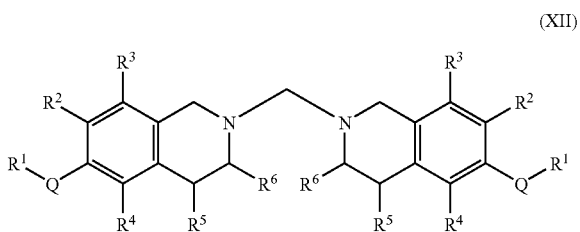

wherein
Q is selected from the group consisting of O and S;
R¹ is $C_{1-6}$alkyl; wherein the $C_{1-6}$alkyl is optionally substituted with one or more substituents independently selected from halogen, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino, aryl, cycloalkyl, heteroaryl or heterocycloalkyl;
wherein the aryl, cycloalkyl, heteroaryl or heterocycloalkyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;
R² is selected from the group consisting of hydrogen, hydroxy, $C_{1-6}$alkyl, $C_{1-6}$alkoxy, aryl, cycloalkyl, heteroaryl or heterocycloalkyl;
wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 7-position of the 1,2,3,4-tetrahydroisoquinoline core;
alternatively, Q, R¹ and R² are taken together with the carbon atoms to which they are bound to form a 5 to 8 membered, monocyclic heterocycloalkyl group, wherein the 5 to 8 membered, monocyclic heterocycloalkyl optionally contains one additional heteroatom selected from O, N or S, provided that the N is not bound directly to the 7-position of the 1,2,3,4-tetrahydroisoquinoline core;
wherein the 5 to 8 membered monocyclic heterocycloalkyl is optionally substituted with one or more substituents independently selected from halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;

R³ and R⁴ are each independently selected from the group consisting of hydrogen, hydroxy, $C_{1-6}$alkyl, $C_{1-6}$alkoxy, aryl, cycloalkyl, heteroaryl or heterocycloalkyl;
wherein the $C_{1-6}$alkyl, $C_{1-6}$alkoxy, aryl, cycloalkyl, heteroaryl or heterocycloalkyl is optionally substituted with one or more substituents independently selected from the group consisting of hydroxy, $C_{1-4}$alkyl, halogenated $C_{1-4}$alkyl, $C_{1-4}$alkoxy, halogenated $C_{1-4}$alkoxy, amino, $C_{1-4}$alkylamino, di($C_{1-4}$alkyl)amino and halogen; provided that the halogen is not bound to a carbon atom that is bound directly to the 5- or 8-position of the 1,2,3,4-tetrahydroisoquinoline core;
R⁵ and R⁶ are each independently selected from the group consisting of hydrogen, hydroxy, $C_{1-6}$alkyl, halogenated $C_{1-6}$alkyl, $C_{1-6}$alkoxy, halogenated $C_{1-6}$alkoxy, amino, $C_{1-4}$alkylamino, di($C_{1-4}$alkyl)amino, aryl, cycloalkyl, heteroaryl or heterocycloalkyl;
wherein the $C_{1-6}$alkyl, $C_{1-6}$alkoxy, aryl, cycloalkyl, heteroaryl or heterocycloalkyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, amino, $C_{1-4}$alkylamino and di($C_{1-4}$alkyl)amino;
comprising

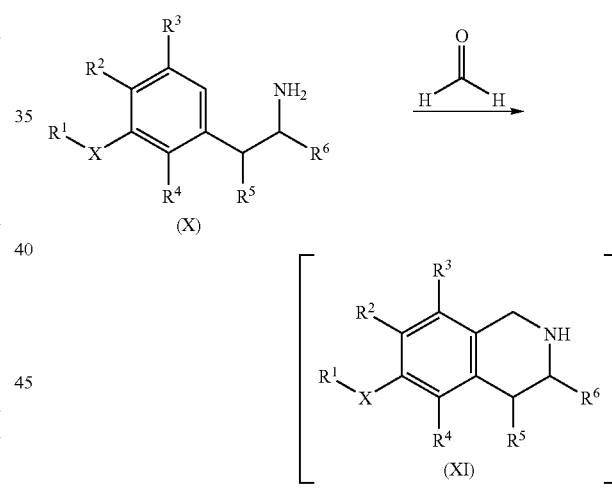

reacting a compound of formula (X) with formaldehyde, in the presence of an inorganic acid, in water or a mixture of water and an alcohol, to yield the corresponding compound of formula (XI), which is not isolated; and

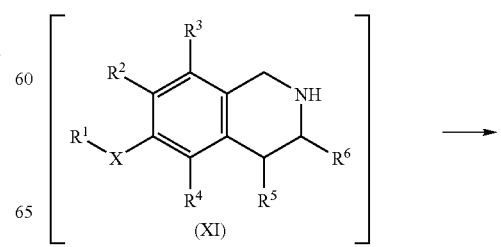

-continued

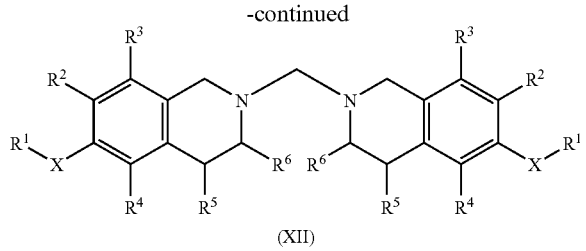

(XII)

treating the reaction mixture containing the compound of formula (XI) with an inorganic base, to yield the corresponding compound of formula (XII), which is isolated.

5. A process as in claim 4, wherein the compound of formula (XII) is isolated by filtration.

6. A process as in claim 4, wherein Q is O, and each of $R^3$, $R^4$, $R^5$ and $R^6$ is hydrogen.

7. A process as in claim 4, wherein Q is O, $R^1$ is methyl, $R^2$ is selected from the group consisting of hydrogen or methoxy; or Q, $R^1$ and $R^2$ are taken together with the carbon atoms to which they are bound to form 1,3-dioxolanyl; and each of $R^3$, $R^4$, $R^5$ and $R^6$ is hydrogen.

* * * * *